United States Patent [19]

Neidlinger et al.

[11] Patent Number: 4,659,590

[45] Date of Patent: Apr. 21, 1987

[54] PERVAPORATION SEPARATION OF ETHANOL-WATER MIXTURES USING POLYETHYLENIMINE COMPOSITE MEMBRANES

[75] Inventors: Hermann H. Neidlinger, Lakewood; Paul O. Schissel, Golden; Richard A. Orth, Denver, all of Colo.

[73] Assignee: United States Department of Energy, Washington, D.C.

[21] Appl. No.: 746,592

[22] Filed: Jun. 19, 1985

[51] Int. Cl.[4] .................... B01D 25/04; B01D 29/46; B05D 4/18; B05D 5/00
[52] U.S. Cl. .................... 427/244; 210/491; 210/500.27; 210/500.41; 427/340; 427/430.1
[58] Field of Search .................... 210/490, 491, 500.2, 210/500.27, 500.41; 427/244, 340, 430.1

[56] References Cited

U.S. PATENT DOCUMENTS 3,951,815  4/1976  Wrasidlo .................... 528/424 X
4,039,440  8/1977  Cadotte .................... 210/500.2

*Primary Examiner*—Michael R. Lusignan
*Attorney, Agent, or Firm*—Kenreth L. Richardson; James W. Weinberger; Judson R. Hightower

[57] ABSTRACT

Synthetic, organic, polymeric membranes were prepared from polyethylenimine for use with pervaporation apparatus in the separation of ethanol-water mixtures. The polymeric material was prepared in dilute aqueous solution and coated onto a polysulfone support film, from which excess polymeric material was subsequently removed. Cross-links were then generated by limited exposure to toluene-2,4-diisocyanate solution, after which the prepared membrane was heat-cured. The resulting membrane structures showed high selectivity in permeating ethanol or water over a wide range of feed concentrations.

7 Claims, No Drawings

PERVAPORATION SEPARATION OF ETHANOL-WATER MIXTURES USING POLYETHYLENIMINE COMPOSITE MEMBRANES

CONTRACTUAL ORIGIN OF THE INVENTION

The United States Government has rights in this invention under Contract No. DE-AC02-83CH10093 between the United States Department of Energy and the Solar Energy Research Institute, a division of the Midwest Research Institute.

BACKGROUND OF THE INVENTION

1. Field of the Invention

The invention generally relates to liquid purification or separation. More specifically, the invention relates to membrane materials for separation of ethanol and water mixtures. The invention also relates generally to coating processes in which a permselective product is produced, specifically a thin, dense coating on a microporous substrate.

2. Description of the Prior Art

Ethanol is commonly produced by fermentation processes, wherein the ethanol product is found in a water mixture. The production of fuel-grade ethanol requires that the fermentation product be dried beyond the azeotrope. The usual drying process of distillation requires a significant amount of energy. Therefore, it is desirable to separate ethanol from fermentation beers by a more economical method, such as by membrane separation. In addition, significant preferential passage of ethanol at feed concentrations corresponding to fermentation beers can be a significant result because it may permit a fermentation process to operate at a low ethanol concentration while yielding a pervaporate sufficiently enriched for further processing by distillation or other means.

Selective membranes have been used in reverse osmosis processes, such as in the desalination of seawater and the separation of azeotropic mixtures of aromatic and aliphatic hydrocarbons or close boiling isomers. A principle disadvantage of reverse osmosis is that a high pressure is needed in excess of the prevailing osmotic pressure to drive the permeate through the membrane. Prevaporation avoids the limitation of osmotic pressure imposed on reverse osmosis processes by maintaining the permeate below its saturated vapor pressure. The heat of vaporization must be supplied to the permeating fraction in pervaporation, whereas during reverse osmosis there is no phase change and the heat of vaporization is not required. Thus, membranes used in the pervaporation process must meet more stringent membrane performance. To minimize energy input, membranes that pass water selectively would be of importance for solutions concentrated in ethanol, while membranes that pass ethanol selectively could remove ethanol directly from a fermentation bath. In either of these concentration regimes, osmotic pressures would hinder the competitive use of reverse osmosis.

The membrane separation of ethanol from water is difficult, and those membranes used for the separation of ethanol from either simple aqueous mixtures or from fermentation beers using reverse osmosis or pervaporation have been successful usually only in achieving a permeate that is enriched in water. A small number of exceptions to this result have been noted in published literature, as follows. It is reported in Heisler, E. G., A. S. Hunter, J. Siciliano, R. H. Treadway, *Science*, Vol. 124, p. 77, 1956, that adding benzoic acid to the feed yielded a slight enrichment of ethanol in the permeate when used with a cellophane membrane. Eustache, H., and G. Histi, *J. Membr. Sci.*, Vol. 8, p. 105, 1981, report the use of pervaporation with a membrane of polydimethylsiloxane to yield a permeate enriched in ethanol. However, the latter measurements used feeds of only very low ethanol concentrations (ca. 0.1–1.0%). Finally, Hoover, K. C., and S. T. Hwang, *J. Membr. Sci.*, Vol. 10, p. 253, 1982, report the use of a silicone rubber membrane in a pervaporation column with good separation factors at low ethanol concentrations; however, there was essentially no separation at very high ethanol concentrations. Thus, the prior art has not produced a membrane that is well suited to the separation of ethanol from water over a wide range of concentrations.

A primary problem encountered in membrane technology used to separate ethanol from water mixtures remains the creation of a membrane material that optimizes the properties that permit high separation efficiency and permeability. Some of the factors that influence the permeation process is polymers include chemical composition, membrane homogeneity, and the imposed driving forces causing permeation. It remains unpredictable as to what membrane composition will best perform in these areas, as the mechanism or mechanisms of membrane separation remain somewhat controversial, although the general sorption-diffusion theory is supported by a growing body of evidence.

The efficiency of liquid permeation separations through polymer films depends primarily on whether there is an interaction, chemical or physical, between the solvent, solute, and polymer. The extent of the liquid-polymer interaction determines how swollen the polymer becomes. These interactions arise in general from polar-, steric-, nonpolar-, or ionic-character of each of the above three components in the membrane system. The overall result of their interactions determines whether solvent, solute, or neither is preferentially sorbed at the membrane-solution interface.

Further, it has been observed that the permselectivity of a polymeric material increases as the general level of flux rate decreases. This aspect of transport behaviour must be overcome for economic separation processes by appropriate changes in membrane geometry and by adjusting polymer composition, structure, and morphology to enhance transport behaviour of the chosen penetrant. Both the diffusion coefficient and solubility coefficient of a penetrant are quite sensitive to minor variations in polymer composition and structure, which provides a possibility to experimentally derive useful permselective membrane materials.

Changes in membrane geometry are of great importance, as flux is inversely dependent on film thickness, while permeability constants are independent of thickness. Consequently, a very thin film can be highly permselective with excellent overall fluxes of the desired penetrant species. However, the presence and damaging effects of pinholes or other defects increase with decreasing membrane thickness. In order to develop optimum thin film materials, it is therefore essential that the dependence of permeability on factors that control transport processes be understood.

The above noted factors, among others, demonstrate the difficulty faced in the development of a membrane having the combination of high selectivity and concurrent high flux of the premeating species. To achieve the foregoing and other objects and in accordance with the purpose of the present invention, as embodied and broadly described herein, the membrane and method of manufacture of this invention may comprise the following.

SUMMARY OF THE INVENTION

Against the described background, it is therefore a general object of the invention to provide a permselective membrane for water or ethanol.

Another general object of the invention is to provide a membrane adapted to separate water-ethanol mixtures with a combination of high selectivity and concurrent high flux of the permeating species.

A more specific object is to provide a synthetic, organic, polymeric membrane that permeates water or ethanol over a wide range of feed compositions in order to obtain a more highly concentrated water-ethanol solution.

Another specific object is to provide a process for making a membrane capable of efficiently permeating at least a portion of the water or ethanol from a feed solution in a prevaporation process.

Additional objects, advantages and novel features of the invention shall be set forth in part in the description that follows, and in part will become apparent to those skilled in the art upon examination of the following or may be learned by the practice of the invention. The object and the advantages of the invention may be realized and attained by means of the instrumentalities and in combinations particularly pointed out in the appended claims.

In a process for preparing a composite membrane capable of selectively permeating water or ethanol from a water-ethanol mixture, an aqueous solution is prepared of a synthetic, organic, polymeric substance of ethylenimine. Then, a microporous support member is coated with the prepared aqueous solution for a predetermined time sufficient to deposit a uniform coating of the polymeric substance on the support member. Thereafter, the surface of the polymeric substance is cross-linked by treating the surface with a cross-linking agent for a predetermined time, after which the membrane is heat-cured.

According to another aspect of the invention, a permeation apparatus is provided, having a microporous support member, a coating on the support member of a synthetic, organic, polymeric substance characterized by the presence of ethylenimine groups, and a partially cross-linked surface network on the coating.

DESCRIPTION OF THE PREFERRED EMBODIMENTS

Synthetic organic polymeric membranes were developed that separate ethanol-water mixtures over a wide range of ethanol-water feed compositions. The membranes are characterized by the presence of a polymer group consisting of ethylenimine. In each case, the process of testing the membranes involved contacting a liquid feed mixture of ethanol and water against one side of a membrane and withdrawing at the second side a vapor phase mixture having a higher concentration of ethanol or water than was present in the feed mixture.

Membrane performance was measured and calculated to determine relevant parameters relating to performance with ethanol (e) or water (w). The diffusion flow or flux, $J_w$, of substance w through a film is defined as the amount passing during a unit time through a surface of unit area normal to the direction of flow.

A separation factor $SFa_w$ for substance w in a system of two penetrants in a pervaporation process is defined as the ratio of the permeability constants of each penetrant in the membrane when the downstream pressure is close to zero, according to the equation:

$$SFa_w = P_w/P_e$$

where P is the permeability constant for the respective substance w or e and is defined by the product of the solubility coefficient and the diffusion coefficient for the respective substance.

An alternative separation factor $SFb_w$ is defined as:

$$SFb_w p_w/f_w$$

where p is the weight fraction of the substance w in the downstream phase (permeate) and $f_w$ is the weight fraction of the substance w in the upstream phase (feed). For a w selective membrane, $SFa_w$ will be greater than $SFb_w$.

The efficiency or productivity factor of a pervaporator equipped with a given w-selective membrane can be derived to be proportional to the product:

$$(SFb_w - 1)J$$

where J is the permeate flux.

Efficient and selective polymeric membranes were prepared from ethylenimine by dissolving the appropriate polymeric substance in water to a predetermined concentration, dip-coating a microporous support in the aqueous solution, applying a cross-linking agent to the treated support for a time sufficient to achieve a predetermined degree of cross-linking in the membrane surface, and heat curing.

The membrane support member was chosen for its ability to carry the polymeric membranes without interfering with or contributing to the separation. A polysulfone film was selected as the preferred support film, as an uncoated polysulfone film does not exhibit may selectivity in a water-ethanol system and, due to its microporosity, has a large flux of about 50 L/m²h.

The polymeric substances were dissolved in aqueous solution in order to obtain a desired film thinness and uniformity by the dip-coating process. It has been found that concentrations of less than about 2% by weight are suitable, with the preferred concentration being on the order of 0.5-2% for polyethylenimine and preferably less than about 1.4% in order to produce a membrane that has the desired thinness and uniformity. After the coating is applied to the support, a limited degree of cross-linking is desired to establish a cross-linked polymeric coating over the surface of the supported membrane structure. A suitable cross-linking agent such as toluene-2,4-diisocyanate in a hexane solution may be used to achieve the limited cross-linking by an interfacial addition reaction. Exposure for approximately one minute is adequate to achieve the desired cross-linked surface on the polymeric film.

The composite membrane is cured after cross-linking by drying in an oven at a temperature from 100° C. to 150° C. The curing process also removes residual water and hexane from the polymer and its supporting structure.

The membrane may be a simple disk or sheet of the membrane substance. However, other forms of membrane may also be employed, such as hollow tubes and fibers. Various other shapes and sizes are readily adaptable to commercial installations.

Synthetic organic polymeric membranes characterized by the presence of ethylenimine groups were produced and evaluated. The membranes were prepared in 25 different variations, as illustrated in the following examples.

EXAMPLE 1

Composite membrane PEI-1 was prepared by, first, dissolving polyethylenimine (PEI) in water to form an aqueous 0.68% by weight PEI solution. Then, a polysulfone support film was dip-coated into the aqueous PEI solution by soaking for about ten minutes to form a thin membrane of uniform thickness. After draining for one minute, the support film was further dipped into a 0.5% by weight toluene-2,4-diisocyanate (TDI) solution in hexane for one minute to generate cross-links through an interfacial film reaction. The prepared membrane was then heat-cured in a convection oven at 110° C. for 10 minutes.

Membrane performance was evaluated in a pervaporation apparatus that consists of a constant temperature bath and pump that circulates the feed through a radial-flow cell at a rate of about 1.4 L/min and with bath temperatures controlled to 0.1° C. The membrane is mounted on a porous plate of stainless steel embedded in the membrane cell. A downstream compartment consists of two parallel pumping stations that allow alternate sampling from cold traps. Five centimeter diameter pumping lines connect to the lower surface of the membrane to ensure that pressures downstream are well below the saturated vapor pressures even for membranes passing up to 170 L/m²h. A thermocouple gauge located immediately downstream from the membrane was used as a semiquantitive monitor of the permeate pressure. Pervaporation data are as shown in Table 1, below.

The separation factors $SFa_w$ and $SFb_w$ for PEI-1 were found to be dependent upon feed composition. Specifically, it was found that membrane PEI-1 permeates ethanol selectively between approximately 12% (w/w) and 62% (w/w) ethanol feed composition and permeates water selectively below 12% (w/w) and above 62% (w/w).

The productivity parameter $(SFb_w-1)J$ demonstrates that the efficiency of this membrane increases with increasing ethanol concentration in the regimes where water selectivity is exhibited. In the ethanol selective range, efficiency was found to be highest around 45% ethanol.

TABLE 1

| | PERVAPORATION MEASUREMENTS, PEI-1 MEMBRANE | | | | | | | | |
|---|---|---|---|---|---|---|---|---|---|
| Run No. | Ethanol w-fraction | | Permeation | | Temp. (°C.) | Pressure (Torr) | $SFa_w$ | $SFb_w$ | J (L/m²h) | $(SFb_w - 1)J$ |
| | Feed | Permeate | Vol. (mL) | Time (h) | | | | | | |
| 1 | 0.045 | 0.013 | 1.8 | 3 | 23 | 0.04 | 3.6 | 1.03 | 0.15 | 0.005 |
| 2 | 0.043 | 0.023 | 6 | 3 | 33 | 0.05 | 1.9 | 1.02 | 0.51 | 0.01 |
| 3 | 0.041 | 0.028 | 9.8 | 3 | 43 | 0.07 | 1.5 | 1.01 | 0.83 | 0.01 |
| 4 | 0.192 | 0.266 | 16 | 3 | 43 | 0.07 | 1.4[a] | 1.32[b] | 1.36 | 0.44[c] |
| 5 | 0.336 | 0.416 | 24 | 3 | 43 | 0.09 | 1.4[a] | 1.25[b] | 2.04 | 0.51[c] |
| 6 | 0.408 | 0.460 | 26 | 3 | 43 | 0.09 | 1.3[a] | 1.16[b] | 2.21 | 0.35[c] |
| 7 | 0.973 | 0.925 | 27 | 3 | 43 | 0.09 | 2.9 | 2.78 | 2.30 | 4.09 |
| 8 | 0.453 | 0.568 | 30 | 3 | 43 | 0.09 | 1.7[a] | 1.29[b] | 2.55 | 0.74[c] |
| 9 | 0.849 | 0.759 | 30 | 2.5 | 43 | 0.14 | 1.8 | 1.60 | 3.06 | 1.82 |
| 10 | 0.745 | 0.697 | 53 | 4.5 | 43 | 0.14 | 1.3 | 1.19 | 3.00 | 0.57 |

[a] $SFa_e$
[b] $SFb_e$
[c] $(SFb_e - 1)J$

Various modifications of this preparation procedure were evaluated in Examples 2-6. Pervaporation studies were performed on these membranes using selected ethanol feed solutions, with the results shown in Table 2, below.

EXAMPLE 2

Composite membrane PEI-2 was prepared according to the techniques of Example 1, with the addition of a drying step (in vacuo) after immersion into the PEI solution.

The resulting data show no significant change in separation properties as a result of the vacuum drying before cross-linking with TDI. Flux was somewhat higher for high ethanol feeds in comparison to those for the membrane prepared in Example 1.

EXAMPLE 3

Composite membrane PEI-3 was prepared by treating a membrane prepared according to Example 1 with an aqueous 5% glyoxal solution at 90° C. for 60 minutes and then drying and heat-curing in a convection oven at 110° C. for 10 minutes.

The resulting data show no significant change in separation properties as compared to the results from Example 1, although total flux was slightly decreased.

EXAMPLE 4

Composite membrane PEI-4 was prepared by treating a membrane prepared according to Example 2 with an aqueous 5% glyoxal solution at 90° C. for 60 minutes and then drying and heat-curing in a convection oven at 110° C. for 10 minutes.

The resulting data show no significant chaange in separation properties by the combination of vacuum drying before cross-linking, glyoxal treatment, and then heat curing. Flux was somewhat higher for high ethanol feeds in comparison to those of the membrane described in Example 1.

The lack of significant change in selectivity for PEI-4 raised the possibility that the TDI cross-linking reaction resulted in blocking most of the reactive amine groups and thus preventing an extensive glyoxal attachment. In order to avoid this problem, membranes were prepared as illustrated in the following examples 5 and 6.

Example 5. Composite membrane PEI-5 was fabricated by immersing a polysulfone support film into an aqueous 0.68% PEI solution for 10 minutes. The coated film was vacuum dried, then treated with an aqueous 5% glyoxal solution at 90° C. for 60 minutes, and dried and heat-cured in a convection oven at 110° C. for 10 minutes.

Example 6. Composite membrane PEI-6 was prepared by modifying the preparation technique for PEI-5 by substituting an aqueous 25% glutaric aldehyde solution for the glyoxal solution under otherwise the same reaction conditions.

TABLE 2

PERVAPORATION MEASUREMENTS, PEI-2 THRU PEI-6, T = 43° C.

| Run No. | Ethanol w-fraction Feed | Ethanol w-fraction Permeate | Permeation Vol. (mL) | Permeation Time (h) | Pressure (Torr) | $SFa_w$ | $SFb_w$ | J ($L/m^2h$) | $(SFb_w - 1)J$ |
|---|---|---|---|---|---|---|---|---|---|
| PEI-2 | | | | | | | | | |
| 11 | 0.286 | 0.412 | 23 | 3 | 0.09 | $1.79^a$ | $1.46^b$ | 1.96 | $0.90^c$ |
| 12 | 0.256 | 0.360 | 20 | 3 | 0.09 | $1.59^a$ | $1.38^b$ | 1.70 | $0.65^c$ |
| 13 | 0.969 | 0.934 | 40 | 3 | 1.4 | 2.22 | 2.13 | 3.40 | 3.84 |
| PEI-3 | | | | | | | | | |
| 14 | 0.966 | 0.910 | 29 | 4 | 0.09 | 2.86 | 2.65 | 1.85 | 3.05 |
| PEI-4 | | | | | | | | | |
| 15 | 0.965 | 0.925 | 40 | 3 | 0.13 | 2.27 | 2.14 | 3.40 | 3.88 |
| 16 | 0.440 | 0.527 | 28 | 2 | 0.14 | $1.19^a$ | $1.10^b$ | 3.57 | $0.35^c$ |
| PEI-5 | | | | | | | | | |
| 17 | 0.456 | 0.305 | 16 | 2 | 0.1 | 1.92 | 1.28 | 2.04 | 0.57 |
| 18 | 0.972 | 0.910 | 14 | 3 | 0.08 | 3.45 | 3.21 | 1.19 | 2.63 |
| PEI-6 | | | | | | | | | |
| 19 | 0.972 | 0.890 | 0.5 | 5 | 0.02 | 4.2 | 3.93 | 0.026 | 0.076 |
| 20 | 0.066 | 0.017 | 1.5 | 3 | 0.03 | 4.0 | 1.05 | 0.128 | 0.007 |
| 21 | 0.432 | 0.121 | 1 | 4 | 0.02 | 5.56 | 1.55 | 0.064 | 0.035 |

$^a SFa_c$
$^b SFb_c$
$^c (SFb_c - 1)J$

The pervaporation results for membranes PEI-5 and PEI-6 show a higher water selectivity but also considerably decreased fluxes in comparison to PEI-1. Such increased selectivity with corresponding reduction of flux may also be obtained from membrane PEI-1 by operation at lower evaluation temperatures.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

The embodiments of the invention in which an exclusive property or privilege is claimed are defined as follows:

1. The method of separating an ethanol-water mixture through a membrane film, comprising:
   providing a polymeric membrane film having a first and second side and consisting essentially of ethylenimine polymers supported on a microporous member and having a partially cross-linked and heat-cured surface, said cross-linking having been achieved by the use of a cross-linking agent consisting essentially of an isocyanate compound;
   providing an ethanol-water feed solution on said first side of said membrane film;
   applying a pressure differential between said first and said second sides of said membrane film sufficient to induce a diffusion flow of a permeate from the feed solution through said membrane; and
   recovering said permeate on said second side of said membrane film.

2. The method of claim 1, wherein said feed solution comprises ethanol between approximately 12% and 62% by weight, and said permeate comprises a relatively increased weight fraction of ethanol.

3. The method of claim 1, wherein said feed solution comprises ethanol in the ranges of less than approximately 12% and greater than approximately 62% by weight, and said permeate comprises, respectively, a relatively decreased weight fraction of ethanol.

4. The method of claim 1, wherein said membrane film is formed by the process comprising:
   soaking said microporous support member in an aqueous solution of a coating material for a time sufficient to deposit a uniform coating layer on said support member, wherein said coating material consists essentially of ethylenimine polymers;
   removing drainable aqueous solution from said coated support member;
   exposing said coated support member to a cross-linking agent consisting essentially of an isocyanate compound for a time sufficient to form a partially cross-linked surface network with the coating material; and then
   applying heat in quantity and for a time sufficient to cure the network.

5. The method of claim 4, wherein said aqueous solution is no more than about 2% by weight ethylenimine groups.

6. The method of claim 4, wherein said aqueous solution is no more than about 1.4% by weight ethylenimine groups.

7. The method of claim 5, wherein said cross-linking agent comprises 0.5% by weight toluene-2,4-diisocyanate applied to the surface of said coating for about 1 minute.

* * * * *